United States Patent [19]

Cesa et al.

[11] Patent Number: 4,977,272
[45] Date of Patent: Dec. 11, 1990

[54] OLEFINIC N,N'-DISUBSTITUTED UREAS

[75] Inventors: Mark C. Cesa, South Euclid; James E. Rinz, University Heights; Gilles Klopman, East Cleveland; Teodora T. Kopp, Garfield Heights, all of Ohio

[73] Assignee: The Standard Oil Company, Cleveland, Ohio

[21] Appl. No.: 372,996

[22] Filed: Jun. 29, 1989

Related U.S. Application Data

[62] Division of Ser. No. 197,711, May 23, 1988.

[51] Int. Cl.$^5$ .................. C07D 403/00; C07D 233/54; C07D 209/10; C07C 229/00
[52] U.S. Cl. .................... 548/336; 548/341; 548/342; 548/455; 548/467; 548/468; 548/495; 548/496; 548/506; 548/507; 548/511; 558/230; 558/251; 558/254; 260/404.5
[58] Field of Search ............ 560/34, 16, 251; 548/336, 341, 342, 455, 467, 468, 495, 496, 506, 507, 511; 558/230, 251, 254; 260/404.5 R Primary Examiner—Glennon H. Hollrah
Assistant Examiner—Peter G. O'Sullivan
Attorney, Agent, or Firm—C. S. Lynch; D. J. Untener; L. W. Evans

[57] ABSTRACT

This invention relates to new compounds of the formula:

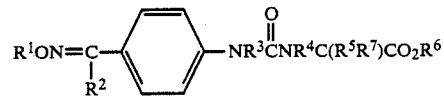

where each of $R^1$, $R^2$, $R^3$, $R^4$, $R^5$, $R^6$ and $R^7$ has zero to 10 C atoms, and no acetylenic unsaturation; each of $R^1$, $R^2$, $R^3$ and $R^4$ is independently selected from H and hydrocarbyl; with the proviso that $R^6$ is $C_1$–$C_{10}$ hydrocarbyl; each of $R^5$ and $R^7$ is independently selected from H, hydrocarbyl and hydrocarbyl substituted with a group selected from:

hydrocarbylcarbonylamino, di(hydrocarbylcarbonyl)amino, N-hydrocarbylcarbonyl(N-hydrocarbyl)amino, formylamino, diformylamino, and formyl(N-hydrocarbyl)amino, hydrocarbyloxy, hydrocarbylthio, formyl, formylthio, hydrocarbylcarbonyloxy, hydrocarbylcarbonylthio, hydrocarbyl carboxyl, hydrocarbyl thiocarboxyl, hydrocarbylamino, dihydrocarbylamino, hydrocarbylcarbonyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, and 5-(3-formyl)imidazolyl; and where at least one of $R^1$, $R^2$, $R^3$, $R^4$, $R^5$, $R^6$ and $R^7$ contains olefinic unsaturation. The invention also relates to addition polymers of such compounds.

1 Claim, No Drawings

OLEFINIC N,N'-DISUBSTITUTED UREAS

This invention relates to new compounds of the formula:

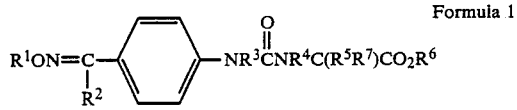

Formula 1 where each of $R^1$, $R^2$, $R^3$ $R^4$, $R^5$, $R^6$ and $R^7$ has zero to 10 C atoms, and no acetylenic unsaturation; each of $R^1$, $R^2$, $R^3$ and $R^4$ is independently selected from H and hydrocarbyl; with the proviso that $R^6$ is $C_1$–$C_{10}$ hydrocarbyl; each of $R^5$ and $R^7$ is independently selected from H, hydrocarbyl and hydrocarbyl substituted with a group selected from:
hydrocarbylcarbonylamino, di(hydrocarbylcarbonyl)amino, N-hydrocarbylcarbonyl(N-hydrocarbyl)amino, formylamino, diformylamino, and formyl(N-hydrocarbyl)amino, hydrocarbyloxy, hydrocarbylthio, formyl, formylthio, hydrocarbylcarbonyloxy, hydrocarbylcarbonylthio, hydrocarbyl carboxyl, hydrocarbyl thiocarboxyl, hydrocarbylamino, dihydrocarbylamino, hydrocarbylcarbonyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, hydrocarbyl)imidazolyl, 5-(3-hydrocarbylcarbonyl)imidazolyl, and 5-(3-formyl)imidazolyl;
and where at least one of $R^1$, $R^2$, $R^3$, $R^4$, $R^5$, $R^6$ and $R^7$ contains olefinic unsaturation. The invention also relates to addition polymers of such compounds.

These compounds are useful ultraviolet light absorbers. They can be used in plastic compositions to impart this property. It is believed that the excellent UV light absorption of these compounds is related to the fact that the compounds of the invention have the oxime, arene, and urea chromophores in conjugation. Such structures are believed to be novel.

The compounds of the invention all have high molar extinction coefficients, $\lambda_{max}$=250-290 nm, $\epsilon \geq 10^4$. In our work the particular solvent used in measuring the absorbance to determine the extinction coefficients is methanol.

The products of the present invention where at least one of $R^1$, $R^5$, $R^6$ and $R^7$ contains an olefinic group and where $R^2$, $R^3$, and $R^4$ are H can be prepared by reacting the compound

Formula 2 with an acetal of 4-aminobenzaldehyde derived from a $C_1$ to $C_6$ monoalkanol or a $C_1$ to $C_6$ alkanediol, said reaction being carried out in a solvent such as dioxane, THF, diethyl ether, glymes and di-n-butyl ether in the presence of a non-nucleophilic base, and then reacting the product of such reaction with hydroxylamine hydrochloride in methanol as the solvent to obtain the compound of Formula 1 where $R^1$ is H. The acetal can be prepared by first making the acetal of 4-nitrobenzaldehyde and then hydrogenating such acetal over platinum oxide catalyst to make the corresponding 4-aminobenzaldehyde, as illustrated in the specific examples. To prepare a product with $R^1$ containing an olefinic group, the compound of Formula 1 where $R^1$ is H is then treated with a solution of sodium methoxide in methanol, then with a $C_2$–$C_{10}$ olefinic halide such as allyl bromide or crotyl bromide, to prepare the product compound of Formula 1 where $R^1$ contains olefinic unsaturation.

The products of the present invention where at least one of $R^1$ $R^5$, $R^6$, and $R^7$ contains an olefinic group and where $R^2$ is hydrocarbyl and where $R^3$ and $R^4$ are H can be made by reacting the compound of Formula 2 with

Formula 3 in one of the same solvents (dioxane, THF, etc.) to obtain

Formula 4 which is then separated from the solvent. This product is reacted in methanol solvent with hydroxylamine hydrochloride to obtain the compound of Formula 1 where $R^1$ is H. To prepare a product in which $R^1$ contains an olefinic group, this compound is then treated with a solution of sodium methoxide in methanol, then with a $C_2$–$C_{10}$ olefinic halide such as allyl bromide or crotyl bromide, to prepare he product compound of Formula 1 where $R^1$ contains olefinic unsaturation.

Compounds of Formula 1 where $R^3$ contains an olefinic group and where $R^2$ and $R^4$ are H can be prepared by reacting

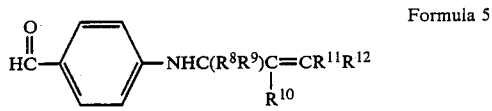

Formula 5 where $R^8$, $R^9$, $R^{10}$, $R^{11}$ and $R^{12}$ are independently selected from H and alkyl such that the total number of carbon atoms in $R^8$, $R^9$, $R^{10}$, $R^{11}$ and $R^{12}$ is less than or equal to 7, with a $C_1$ to $C_6$ monoalkanol or a $C_1$ to $C_6$ alkanediol to form an acetal, then reacting said acetal with a compound of Formula 2 in a solvent such as dioxane, THF, diethyl ether, glymes, and di-n-butyl ether in the presence of a non-nucleophilic base, and then reacting the product of such reaction with hydroxylamine hydrochloride in methanol as the solvent to obtain the compound of Formula 1.

The products of the present invention where at least one of $R^4$, $R^5$, $R^6$ and $R^7$ contains an olefinic group can be prepared by reacting

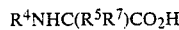   6 with an alcohol $R^6$OH to prepare

   7 then reacting compounds of Formula 7 with

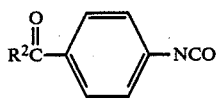

Formula 8 in one of the same solvents (dioxane, THF, etc.) to prepare a compound of Formula 4, which is then separated from the solvent. This product is reacted in methanol solvent with hydroxylamine hydrochloride to obtain the compound of Formula 1.

The isocyanates of Formula 2 can be prepared by reacting the compound

Formula 9 or its salt with diphosgene in the manner illustrated in the examples herein.

In preparing the polymers of the present invention, a monomer of Formula 1 is polymerized in the presence of a polymerization catalyst. Suitable polymerization catalysts include, but are not restricted to, 2,2'-azobis-(isobutyronitrile) (AIBN), di-(tert-butyl)peroxide, benzoyl peroxide, tert-butyl hydrogen peroxide, ammonium persulfate, potassium persulfate, and the like.

Two examples of the usefulness of the present compounds are as follows:

Blow Molded LDPE Bottles 1 part substituted urea compound or polymer is blended with 1000 parts low-density polyethylene in a plasticating screw extruder, pelletized, and blow molded to give a bottle which has substantially reduced UV transparency compared with a bottle made without the urea compound or polymer.

Polyethylene Sheet 1 part substituted urea compound or polymer is blended with 1000 parts low-density polyethylene in a plasticating screw extruder and then extrusion blow molded into a thin film which exhibits substantially reduced UV transparency compared with film not containing the urea compound or polymer.

The following examples are merely illustrative and are not to be considered as limiting.

EXAMPLE 1

4 Nitrobenzaldehyde ethylene glycol acetal is made as follows: A mixture of 75.5 g p-nitrobenzaldehyde, 100 mL ethylene glycol, and 2.5 g p-toluenesulfonic acid in 500 mL toluene is heated with stirring to reflux under $N_2$ for 5 hours in a 1000 mL round bottom flask equipped with a Dean-Stark trap and reflux condenser. During this time about 20 mL of a mixture of water and ethylene glycol is collected in the trap. The product mixture is washed with two 100 mL portions of saturated aqueous sodium bicarbonate solution and with 100 mL water. The organic layer is dried over $MgSO_4$, and the solvent is distilled off on a rotary evaporator. The resultant yellow solid is recrystallized from ethanol to give a yellow crystalline solid, mp. 87°–88° C., yield=-80–85%.

4-Aminobenzaldehyde ethylene glycol acetal is made as follows: A mixture of 19.5 g of p-nitrobenzaldehyde ethylene glycol acetal, 21.2 g trimethyl orthoformate, and 2 g $PtO_2$ in 250 mL anhydrous THF is placed in a 450 mL Parr stirred autoclave. The contents are purged with $N_2$, with the contents kept between 7° and 10° C. by external cooling. 100 psig $H_2$ was pressed in, and the reaction mixture is stirred. The reaction mixture warms to 20° C., and external cooling (ice bath) is maintained. The $H_2$ pressure is maintained at 100 psi by repressurization several times over a 14–18 minute period. The temperature then begins to drop, and little further drop in $H_2$ pressure is noted. The reaction mixture is stirred for a total of 45 minutes, after which time the reaction temperature returns to 7°–10° C. The autoclave is vented and opened, and the pale yellow product solution is filtered, dried over $CaSO_4$, refiltered, and distilled to dryness by rotary evaporator. The product p-aminobenzaldehyde ethylene glycol acetal, a nearly white solid, is collected in over 90% yield (mp.=71°–73° C.)

D,L-alanine methyl ester isocyanate is made as follows: 38.8 mL diphosgene is added dropwise over 1 hour to a mixture of 38.92 g DL-alanine methyl ester hydrochloride and 0.4 g activated charcoal in 400 mL dioxane under $N_2$. The reaction mixture warms to 75°–80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give pure DL-alanine methyl ester isocyanate in ~60% yield (b.p. 70° C., 10 mm Hg).

N-[4-(hydroxyiminomethyl)phenyl-N'-(1-methoxycarbonylethyl)urea is prepared as follows: A solution of 0.1 mol of p-aminobenzaldehyde ethylene glycol acetal in 100 mL of anhydrous THF is added dropwise over 10 minutes to a solution of 0.1 mol DL-alanine methyl ester isocyanate and 0.35 mol pyridine in 100 mL THF at room temperature under $N_2$. The yellow reaction mixture is stirred at room temperature for 2 hours. After ½ hour a yellow-orange precipitate begins to form. After 2 hours the solvent is removed by rotary evaporator to give an orange, semisolid mass. A solution of 0.11 mmol hydroxylamine hydrochloride and 0.1 mol trimethyl orthoformate in $CH_3OH$ is added, the reaction mixture is heated to reflux under $N_2$ for 1 hour. The reaction mixture is reduced to about ¼ volume by rotary evaporator, and water is added. White crystals of product form after 2 hours of stirring. The crystals are isolated by filtration and dried overnight in a vacuum oven at 50°–55° C. The yield of product (mp 143°–145.5° C.) is 60%.

A solution of 0.06 mol of N-[4-hydroxyiminomethyl)-phenyl]-N'-(1-methoxycarbonylethyl)urea in 25% methanolic sodium methoxide (0.06 mol) is treated at room temperature with 0.07 mol of allyl bromide. The reaction mixture is stirred until the temperature falls to about 20° C. The reaction mixture is then poured into cold water and extracted with diethyl ether. The ether solution is dried over $MgSO_4$ and filtered, and the solvent is removed by rotary evaporator to yield N-[4-allyloxyiminomethyl)phenyl-N'-(1-methoxycarbonylethyl)urea.

EXAMPLE 2

38.8 mL diphosgene is added dropwise over 1 hour to a mixture of 35 g glycine methyl ester hydrochloride and 0.4 g activated charcoal In 400 ml dioxane under N$_2$. The reaction mixture warms to 80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give pure glycine methyl ester isocyanate in ~70% yield (bp 60° C., 13 mm Hg).

A solution of 0.1 mol of p-aminobenzaldehyde ethylene glycol acetal in 100 mL of anhydrous THF is added dropwise over 10 minutes to a solution of 0.1 mol glycine methyl ester isocyanate and 0.35 mol pyridine in 100 mL THF at room temperature under N$_2$. The yellow reaction mixture is stirred at room temperature for 2 hours. After ½ hour a yellow-orange precipitate begins to form. After 2 hours the solvent is removed by rotary evaporator to give an orange, semisolid mass. A solution of 0.11 mmol hydroxylamine hydrochloride and 0.1 mol trimethyl orthoformate in CH$_3$OH is added, and the reaction mixture is heated to reflux under N$_2$ for 1 hour. The reaction mixture is reduced to about ¼ volume by rotary evaporator, and water is added. Pale yellow crystals of product form, which are isolated by filtration and dried overnight in a vacuum oven at 50°–55° C. The yield of crude product (mp 158°–161° C.): 70–75%. The product is purified by recrystallization from a 10:6:1 solution of CH$_3$OH:H$_2$O: compound. The product is washed with cold water and dried in a vacuum oven at 50° C. to give off-white crystals of N-[4-(hydroxyiminomethyl)phenyl]-N'-methoxycarbonylmethylurea, mp. 167.5°–168.5° C. Elemental analysis: calcd. C 52.59, H 5.22, N 16.72; found C 52.38, H 5.16, N 16.65. $^1$H NMR (acetone-d$_6$): δ10.15 s, 1H, —NOH; 8.4 s, 1H, —NH—; 8.1 s/d, 1H, —CH═N; 7.55 bs, 4H, phenyl; 6.21 s/d, 1H, —NH—; 4.02 s/d, 2H, —CH$_2$—; 3.74 s, 3H, CH$_3$O—. $^{13}$C NMR (acetone-d$_6$): δ172, —COO—; 156, —NCON—; 149, —CH═N—; 119, 128, 142, phenyl; 52, CH$_3$O—; 42, —CH$_2$—. UV-vis (CH$_3$OH): λ$_{max}$=279 nm, ε=2.90×10$^4$.

A solution of 0.07 mol of N-[4-hydroxyiminomethyl)phenyl]-N'-methoxycarbonylmethylurea in 25% methanolic sodium methoxide (0.07 mol) is treated at room temperature with 0.085 mol of allyl bromide. The reaction mixture is stirred until the temperature falls to about 20° C. The reaction mixture is then poured into cold water and extracted with diethyl ether. The ether solution is dried over MgSO$_4$ and filtered, and the solvent is removed by rotary evaporator to yield N-[4-allyloxyiminomethyl)phenyl]-N'-methoxycarbonylmethylurea.

EXAMPLE 3

9.7 mL diphosgene is added dropwise over 50 minutes to a mixture of 12.85 g dimethyl aminomalonate hydrochloride and 0.1 g activated charcoal in 25 mL dioxane under N$_2$. The reaction mixture warms to 75°–80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is purified by fractional distillation (bp 80°–85° C., <1 mm Hg) to give pure dimethyl isocyanatomatonate in >80% yield.

A solution of 0.1 mol of p-aminobenzaldehyde ethylene glycol acetal in 100 mL of anhydrous THF is added dropwise over 10 minutes to a solution of 0.1 mol dimethyl aminomalonate isocyanate and 0.35 mol pyridine in 100 mL THF at room temperature under N$_2$. The yellow reaction mixture is stirred at room temperature for 2 hours. After ½ hour a yellow-orange precipitate begins to form. After 2 hours the solvent is removed by rotary evaporator to give an orange, semisolid mass. A solution of 0.11 mmol hydroxylamine hydrochloride and 0.1 mol trimethyl orthoformate in CH$_3$OH is added, and the reaction mixture is heated to reflux under N$_2$ for 1 hour. The reaction mixture is reduced to about ¼ volume by rotary evaporator, and water is added. White crystals of product form, which were isolated by filtration and dried overnight in a vacuum oven at 50°–55° C. The yield of crude product (mp 164°–166° C.): 75–80%.

The product is purified by multiple extraction with ethanol until the washings are no longer yellow. White crystals of N-[4-(hydroxyiminomethyl)phenyl]-N'-bis(methoxycarbonyl)methylurea result, m.p. 161.5°–162.5° C. Elemental analysis: calcd. C 50.49, H 4.89, N 13.59; found C 50.88, H 4.90, N 13.52. $^1$H NMR (acetone-d$_6$): δ10.95 s, 1H, —NOH; 9.1 s, 1H, —NH—; 7.55 bs, 4H, phenyl; 7.15 d, 1H, —NH—; 5.15 s/d, 1H, —CH—; 3.80 s, 3H, CH$_3$O—. $^{13}$C NMR (acetone-d$_6$): ε168, —COO—; 155, —NCON—; 148, —CH═N—; 118, 128, 142 phenyl; 58 CH$_3$O—; 53 —CH$_2$—. UV-vis (CH$_3$OH): λ$_{max}$=276 nm, ε=3.06×10$^4$.

A solution of 0.07 mol of N-[4-hydroxyiminomethyl)phenyl]-N'-bis(methoxycarbonyl)methylurea in 25% methanolic sodium methoxide (0.07 mol) is treated at room temperature with 0.085 mol of allyl bromide. The reaction mixture is stirred until the temperature falls to about 20° C. The reaction mixture is then poured into cold water and extracted with diethyl ether. The ether solution is dried over MgSO$_4$ and filtered, and the solvent is removed by rotary evaporator to yield N-[4-allyloxyiminomethyl)phenyl]-N'-bis(methoxycarbonyl)methylurea.

EXAMPLE 4

0.35 mol diphosgene is added dropwise over 1 hour to a mixture of 0.28 mol of glycine ethyl ester and 0.4 g activated charcoal in 400 mL dioxane under N$_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give glycine ethyl ester isocyanate.

A solution of 0.1 mol of p-aminobenzaldehyde ethylene glycol acetal in 100 mL of anhydrous THF is added dropwise over 10 minutes to a solution of 0.1 mol of glycine ethyl ester isocyanate and 0.35 mol pyridine in 100 mL THF at room temperature under N$_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in CH$_3$OH is added, and the reaction mixture is heated to reflux under N$_2$ for 1 hour. The reaction mixture is reduced to about ¼ volume by rotary evaporator, and water is added. The product, N-[4-(hydroxyiminomethyl)phenyl-N'-ethoxycarbonylmethylurea, is isolated by filtration and dried in vacuo.

A solution of N-[4-(hydroxyiminomethyl)phenyl]-N'-ethoxycarbonylmethylurea in 25% methanolic sodium methoxide (1.0 equivalent) is treated at room temperature with 1.1 equivalent of crotyl bromide. The reaction mixture is stirred until the temperature falls to about 20° C. The reaction mixture is then poured into cold water and extracted with diethyl ether The ether solution is dried over $MgSO_4$ and filtered, and the solvent is removed by rotary evaporator to yield the corresponding N-[4-crotyloxyiminomethyl)phenyl]-N'-ethoxycarbonylmethylurea.

EXAMPLE 5

0.35 mol diphosgene is added dropwise over 1 hour to a mixture of 0.28 mol of glycine n-propyl ester and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give glycine n-propyl ester isocyanate.

A solution of 0.1 mol of p-aminobenzaldehyde ethylene glycol acetal in 100 mL of anhydrous THF is added dropwise over 10 minutes to a solution of 0.1 mol of glycine n-propyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl]-N'-n-propoxycarbonylmethylurea, is isolated by filtration and dried in vacuo.

A solution of N-[4-(hydroxyiminomethyl)phenyl]-N'-n-propoxycarbonylmethylurea in 25% methanolic sodium methoxide (1.0 equivalent) is treated at room temperature with 1.1 equivalent of crotyl bromide. The reaction mixture is stirred until the temperature falls to about 20° C. The reaction mixture is then poured into cold water and extracted with diethyl ether. The ether solution is dried over $MgSO_4$ and filtered, and the solvent is removed by rotary evaporator to yield the corresponding N-[4-crotyloxyiminomethyl)phenyl]-N'-n-propoxycarbonylmethylurea.

EXAMPLE 6

0.35 mol diphosgene is added dropwise over 1 hour to a mixture of 0.28 mol of glycine isopropyl ester and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is redissolved in 100 mL THF, and the pH of the solution is adjusted to 5.5–6.0 by addition of pyridine. The product mixture is again filtered, and the product is purified by fractional distillation to give glycine isopropyl ester isocyanate.

A solution of 0.1 mol of p-aminobenzaldehyde ethylene glycol acetal in 100 mL of anhydrous THF is added dropwise over 10 minutes to a solution of 0.1 mol of glycine isopropyl ester isocyanate and 0.35 mol pyridine in 100 mL THF at room temperature under $N_2$. The reaction mixture is stirred at room temperature for 2 hours. After 2 hours the solvent is removed by rotary evaporator A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl]-N'-isopropoxycarbonylmethylurea, is isolated by filtration and dried in vacuo.

A solution of N-[4-(hydroxyiminomethyl)phenyl]-N'-isopropoxycarbonylmethylurea in 25% methanolic sodium methoxide (1.0 equivalent) is treated at room temperature with 1.1 equivalent of allyl bromide. The reaction mixture is stirred until the temperature falls to about 20° C. The reaction mixture is then poured into cold water and extracted with diethyl ether. The ether solution is dried over $MgSO_4$ and filtered, and the solvent is removed by rotary evaporator to yield the corresponding N-[4-allyloxyiminomethyl)phenyl]-N'-isopropoxycarbonylmethylurea.

EXAMPLE 7

0.35 mol diphosgene is added dropwise over 1 hour to a mixture of 0.28 mol of glycine tert-butyl ester and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is redissolved in 100 mL THF, and the pH of the solution is adjusted to 5.5–6.0 by addition of pyridine. The product mixture is again filtered, and the product is purified by fractional distillation to give glycine tert-butyl ester isocyanate.

A solution of 0.1 mol of p-aminobenzaldehyde ethylene glycol acetal in 100 mL of anhydrous THF is added dropwise over 10 minutes to a solution of 0.1 mol of glycine tert-butyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl]-N'-tert-butoxycarbonylmethylurea, is isolated by filtration and dried in vacuo.

A solution of N-[4-(hydroxyiminomethyl)phenyl]-N'-tertbutoxycarbonylmethylurea in 25% methanolic sodium methoxide (1.0 equivalent) is treated at room temperature with 1.1 equivalent of allyl bromide. The reaction mixture is stirred until the temperature falls to about 20° C. The reaction mixture is then poured into cold water and extracted with diethyl ether. The ether solution is dried over $MgSO_4$ and filtered, and the solvent is removed by rotary evaporator to yield the corresponding N-[ 4-(allyloxyiminomethyl)phenyl]-N'-tert-butoxycarbonylmethylurea.

EXAMPLE 8

0.35 mol diphosgene is added dropwise over 1 hour to a mixture of 0.28 mol of glycine phenyl ester and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is redissolved in 100 mL THF, and the pH of the solution is adjusted to 5.5–6.0 by addition of pyridine. The product mixture is again filtered, and the product is purified by fractional distillation to give the amino acid methyl ester isocyanate.

TABLE 1

| Example | Amino Acid Methyl Ester | Product |
|---|---|---|
| 9 | valine | N-[4-(allyloxyiminomethyl)phenyl]-N'-(1-methoxycarbonyl)-2-methylpropylurea |
| 10 | leucine | N-[4-(allyloxyiminomethyl)phenyl]-N'-(1-methoxycarbonyl)-3-methylbutylurea |
| 11 | isoleucine | N-[4-(allyloxyiminomethyl)phenyl]-N'-(1-methoxycarbonyl)-1-methylbutylurea |
| 12 | phenylalanine | N-[4-(allyloxyiminomethyl)phenyl]-N'-(1-methoxycarbonyl)-2-phenylethylurea |
| 13 | methionine | N-[4-(allyloxyiminomethyl)phenyl]-N'-(1-methoxycarbonyl)-3-(methylthio)propylurea |
| 14 | O-acetylserine | N-[4-(allyloxyiminomethyl)phenyl]-N'-(1-methoxycarbonyl)-2-acetyloxyethylurea |
| 15 | O-acetylthreonine | N-[4-(allyloxyiminomethyl)phenyl]-N'-(1-methoxycarbonyl)-2-acetyloxypropylurea |
| 16 | S-acetylcysteine | N-[4-(allyloxyiminomethyl)phenyl]-N'-(1-methoxycarbonyl)-2-acetylthioethylurea |
| 17 | (N-acetyl-3-indolyl)alanine | N-[4-(allyloxyiminomethyl)phenyl]-N'-(1-methoxycarbonyl)-2-(N-acetyl-3-indolyl)ethylurea |
| 18 | O-acetyltyrosine | N-[4-(allyloxyiminomethyl)phenyl]-N'-(1-methoxycarbonyl)-2-(4-acetyloxyphenyl)ethylurea |
| 19 | asparagine | N-[4-(allyloxyiminomethyl)phenyl]-N'-(1-methoxycarbonyl)-2-amidoethylurea |
| 20 | glutamine | N-[4-(allyloxyiminomethyl)phenyl]-N'-(1-methoxycarbonyl)-3-amidopropylurea |
| 21 | aspartic acid dimethyl ester | N-[4-(allyloxyiminomethyl)phenyl]-N'-1,2-bis(methoxycarbonyl)ethylurea |
| 22 | glutamic acid dimethyl ester | N-[4-(allyloxyiminomethyl)phenyl]-N'-1,3-bis(methoxycarbonyl)propylurea |
| 23 | ε-N-acetyllysine | N-[4-(allyloxyiminomethyl)phenyl]-N'-(1-methoxycarbonyl)-5-acetamidopentylurea |
| 24 | (3-acetyl-5-imidazolyl)alanine | N-[4-(allyloxyiminomethyl)phenyl]-N'-(1-methoxycarbonyl)-2-(3-acetyl-5-imidazolyl)ethylurea |

A solution of 0.1 mol of p-aminobenzaldehyde ethylene glycol acetal in 100 mL of anhydrous THF is added dropwise over 10 minutes to a solution of 0.1 mol of glycine phenyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl]-N'-phenoxycarbonylmethylurea, is isolated by filtration and dried in vacuo.

A solution of N-[4-(hydroxyiminomethyl)phenyl]-N'-phenoxycarbonylmethylurea in 25% methanolic sodium methoxide (1.0 equivalent) is treated at room temperature with 1.1 equivalent of allyl bromide. The reaction mixture is stirred until the temperature falls to about 20° C. The reaction mixture is then poured into cold water and extracted with diethyl ether. The ether solution is dried over $MgSO_4$ and filtered, and the solvent is removed by rotary evaporator to yield the corresponding N-[4-allyloxyiminomethyl)phenyl]-N'-phenoxycarbonylmethylurea.

EXAMPLES 9–24

For the compounds in Table 1, the following procedure is followed:

0.35 mol diphosgene is added dropwise over 1 hour to a mixture of 0 28 mol of amino acid methyl ester and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is redissolved in 100 mL THF, and the pH of the solution is adjusted to 5.5–6.0 by addition of pyridine. The product mixture is again filtered, and the product is purified by fractional distillation to give the amino acid methyl ester isocyanate.

A solution of 0.1 mol of p-aminobenzaldehyde ethylene glycol acetal in 100 mL of anhydrous THF is added dropwise over 10 minutes to a solution of 0.1 mol of the amino acid methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product N-[4-(hydroxyiminomethyl)phenyl] urea is isolated by filtration and dried in vacuo.

A solution of the N-[4-hydroxyiminomethyl)phenyl] urea in 25% methanolic sodium methoxide (1.0 equivalent) is treated at room temperature with 1.1 equivalent of allyl bromide. The reaction mixture is stirred until the temperature falls to about 20° C. The reaction mixture is then poured into cold water and extracted with diethyl ether. The ether solution is dried over $MgSO_4$ and filtered, and the solvent is removed by rotary evaporator to yield the corresponding N-[4-alkenyloxyiminomethyl)phenyl] urea.

EXAMPLE 25

N-[4-(1-hydroxyiminoethyl)phenyl]-N'-methoxycarbonylmethylurea is made as follows: A solution of 2.7 g p-aminoacetophenone in 40 mL THF is added dropwise to a solution of 2.3 g glycine methyl ester isocyanate and 5 mL pyridine in 40 mL THF, and the reaction mixture is stirred for 3 hours. The solvent is then removed by rotary evaporator to leave an off-white solid. The solid is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to leave an orange oil. Addition of water to the oil results in formation of off-white crystals. The crystals are treated again with 1.0 g hydroxylamine hydrochloride and 3.0 g trimethyl orthoformate in 50 mL CH₃OH at reflux for 1 hour. The product mixture is concentrated by rotary evaporator, water is added, and the solid which forms (mp. 179°–181° C. dec.) was shown by NHR spectroscopy to be pure product, 2.55 g. $^{13}$C NHR (acetone-d₆): δ 172, —COO—; 156, —N-CON—: 142, —C≡N; 118, 127, 131, 153, phenyl: 52, CH₃O—; 42, —CH₂CO—; 12, —CH₃C≡N—. $^1$H NHR (acetone d₆): δ 10.1 s, 1H, —NOH; 8.4 s, 1H, ϕ—N-H—CO—; 7.4–7.6 m, 4H, phenyl; 6.2 t, 1H, —CH₂NH-CO—; 4.0 d, 2H, —NHCH₂—; 3.7 s, 3H, —OCH₃; 2.1 s, 3H, CH₂—C≡N—.

A solution of N-[4-(1-hydroxyiminoethyl)phenyl]-N'-methoxycarbonylmethylurea in 25% methanolic sodium methoxide (1.0 equivalent) is treated at room temperature with 1.1 equivalent of allyl bromide. The reaction mixture is stirred until the temperature falls to about 20° C. The reaction mixture is then poured into cold water and extracted with diethyl ether. The ether solution is dried over MgSO₄ and filtered, and the solvent is removed by rotary evaporator to yield N-[4-(1-allyloxyiminoethyl)phenyl-N'-methoxycarbonylmethylurea.

EXAMPLE 26

A solution of 0.02 mol p-aminoacetophenone in 40 mL THF is added dropwise to a solution of 0.02 mol of glycine ethyl ester isocyanate and 5 mL pyridine in 40 mL THF, and the reaction mixture is stirred for 3 hours. The solvent is then removed by rotary evaporator. The residue is dispersed in 50 mL CH₃OH, and 1.53 g hydroxylamine hydrochloride and 6.4 g trimethyl orthoformate are added. The reaction mixture is heated to reflux for 1 hour. The solvent is removed by rotary evaporator to give N-[4-(1-hydroxyiminoethyl)phenyl]-N'-ethoxycarbonylmethylurea.

A solution of the N-[4-(1-hydroxyiminoethyl)phenyl]-N'-ethoxycarbonylmethylurea in 25% methanolic sodium methoxide (1.0 equivalent) is treated at room temperature with 1.1 equivalent of crotyl bromide. The reaction mixture is stirred until the temperature falls to about 20° C. The reaction mixture is then poured into cold water and extracted with diethyl ether. The ether solution is dried over MgSO₄ and filtered, and the solvent is removed by rotary evaporator to yield the product N-[4-(1-crotyloxyiminoethyl)phenyl]-N'-ethoxycarbonylmethylurea.

EXAMPLE 27

A solution of 0.02 mol p-aminoacetophenone in 40 mL THF is added dropwise to a solution of 0.02 mol of glycine n-propyl ester isocyanate and 5 mL pyridine in 40 ml THF, and the reaction mixture is stirred for 3 hours. The solvent is then removed by rotary evaporator. The residue is dispersed in 50 mL CH₃OH, and 1.53 g hydroxylamine hydrochloride and 6.4 g trimethyl orthoformate are added. The reaction mixture is heated to reflux for 1 hour. The solvent is removed by rotary evaporator to give N-[4-(1-hydroxyiminoethyl)phenyl]-N'-n-propoxycarbonylmethylurea.

A solution of the N-[4-(1-hydroxyiminoethyl)phenyl]-N'-n-propoxycarbonylmethylurea in 25% methanolic sodium methoxide (1.0 equivalent) is treated at room temperature with 1.1 equivalent of crotyl bromide. The reaction mixture is stirred until the temperature falls to about 20° C. The reaction mixture is then poured into cold water and extracted with diethyl ether. The ether solution is dried over MgSO₄ and filtered, and the solvent is removed by rotary evaporator to yield the product N-[4-(1-crotyloxyiminoethyl)phenyl]-N'-n-propoxycarbonylmethylurea.

EXAMPLE 28

A solution of 0.02 mol p-aminoacetophenone in 40 mL THF is added dropwise to a solution of 0.02 mol of glycine isopropyl ester isocyanate and 5 mL pyridine in 40 mL THF, and the reaction mixture is stirred for 3 hours. The solvent is then removed by rotary evaporator. The residue is dispersed in 50 mL CH₃OH, and 1.53 g hydroxylamine hydrochloride and 6.4 g trimethyl orthoformate are added. The reaction mixture is heated to reflux for 1 hour. The solvent is removed by rotary evaporator to give N-[4-(1-hydroxyiminoethyl)phenyl]-N'-isopropoxycarbonylmethylurea.

A solution of the N-[4-(1-hydroxyiminoethyl)phenyl]-N'-isopropoxycarbonylmethylurea in 25% methanolic sodium methoxide (1.0 equivalent) is treated at room temperature with 1.1 equivalent of allyl bromide. The reaction mixture is stirred until the temperature falls to about 20° C. The reaction mixture is then poured into cold water and extracted with diethyl ether. The ether solution is dried over MgSO₄ and filtered, and the solvent is removed by rotary evaporator to yield the product N-[4-(1-allyloxyiminoethyl)phenyl]-N'-isopropoxycarbonylmethylurea.

EXAMPLE 29

A solution of 0.02 mol p-aminoacetophenone in 40 mL THF is added dropwise to a solution of 0.02 mol of glycine tert-butyl ester isocyanate and 5 mL pyridine in 40 mL THF, and the reaction mixture is stirred for 3 hours. The solvent is then removed by rotary evaporator. The residue is dispersed in 50 mL CH₃OH, and 1.53 g hydroxylamine hydrochloride and 6.4 g trimethyl orthoformate are added. The reaction mixture is heated to reflux for 1 hour. The solvent is removed by rotary evaporator to give N-[4-(1-hydroxyiminoethyl)phenyl]-N'-tert-butoxycarbonylmethylurea.

A solution of the N-[4-(1-hydroxyiminoethyl)phenyl]-N'-tertbutoxycarbonylmethylurea in 25% methanolic sodium methoxide (1.0 equivalent) is treated at room temperature with 1.1 equivalent of allyl bromide. The reaction mixture is stirred until the temperature falls to about 20° C. The reaction mixture is then poured into cold water and extracted with diethyl ether. The ether solution is dried over MgSO₄ and filtered, and the solvent is removed by rotary evaporator to yield the product N-[4-(1-allyloxyiminoethyl)phenyl]-N'-tert-butoxycarbonylmethylurea.

EXAMPLE 30

A solution of 0.02 mol p-aminoacetophenone in 40 mL THF is added dropwise to a solution of 0.02 mol of glycine phenyl ester isocyanate and 5 mL pyridine in 40 mL THF, and the reaction mixture is stirred for 3 hours. The solvent is then removed by rotary evaporator. The residue is dispersed in 50 mL CH₃OH, and 1.53 g hydroxylamine hydrochloride and 6.4 g trimethyl orthoformate are added. The reaction mixture is heated to reflux for 1 hour. The solvent is removed by rotary evaporator to give N-[4-(1-hydroxyiminoethyl)phenyl]-N'-phenoxycarbonylmethylurea.

A solution of the N-[4-(1-hydroxyiminoethyl)phenyl]-N'-phenoxycarbonylmethylurea in 25% methanolic sodium methoxide (1.0 equivalent) is treated at room temperature with 1.1 equivalent of allyl bromide.

The reaction mixture is stirred until the temperature falls to about 20° C. The reaction mixture is then poured off on a rotary evaporator to yield 4-(allylamino)benzaldehyde ethylene glycol acetal.

TABLE 2

| Example | Amino Acid Methyl Ester Isocyanate | Product |
| --- | --- | --- |
| 31 | alanine | N-[4-(1-allyloxyiminomethyl)phenyl]-N'-1-methoxycarbonylethylurea |
| 32 | valine | N-[4-(1-allyloxyiminomethyl)phenyl]-N'-(1-methoxycarbonyl)-2-methylpropylurea |
| 33 | leucine | N-[4-(1-allyloxyiminomethyl)phenyl]-N'-(1-methoxycarbonyl)-3-methylbutylurea |
| 34 | isoleucine | N-[4-(1-allyloxyiminomethyl)phenyl]-N'-(1-methoxycarbonyl)-1-methylbutylurea |
| 35 | phenylalanine | N-[4-(1-allyloxyiminomethyl)phenyl]-N'-(1-methoxycarbonyl)-2-phenylethylurea |
| 36 | (N-acetyl-3-indolyl)alanine | N-[4-(1-allyloxyiminomethyl)phenyl]-N'-(1-methoxycarbonyl)-2-(N-acetyl-3-indolyl)-ethylurea |
| 37 | methionine | N-[4-(1-allyloxyiminomethyl)phenyl]-N'-(1-methoxycarbonyl)-3-(methylthio)propylurea |
| 38 | O-acetylserine | N-[4-(1-allyloxyiminomethyl)phenyl]-N'-(1-methoxycarbonyl)-2-acetyloxyethylurea |
| 39 | O-acetylthreonine | N-[4-(1-allyloxyiminomethyl)phenyl]-N'-(1-methoxycarbonyl)-2-acetyloxypropylurea |
| 40 | S-acetylcysteine | N-[4-(1-allyloxyiminomethyl)phenyl]-N'-(1-methoxycarbonyl)-2-acetylthioethylurea |
| 41 | O-acetyltyrosine | N-[4-(1-allyloxyiminomethyl)phenyl]-N'-(1-methoxycarbonyl)-2-(4-acetyloxyphenyl)urea |
| 42 | asparagine | N-[4-(1-allyloxyiminomethyl)phenyl]-N'-(1-methoxycarbonyl)-2-amidoethylurea |
| 43 | glutamine | N-[4-(1-allyloxyiminomethyl)phenyl]-N'-(1-methoxycarbonyl)-3-amidopropylurea |
| 44 | aspartic acid dimethyl ester | N-[4-(1-allyloxyiminomethyl)phenyl]-N'-1,2-bis(methoxycarbonyl)ethylurea |
| 45 | glutamic acid dimethyl ester | N-[4-(1-allyloxyiminomethyl)phenyl]-N'-1,3-bis(methoxycarbonyl)propylurea |
| 46 | ε-N-acetyllysine | N-[4-(1-allyloxyiminomethyl)phenyl]-N'-(1-methoxycarbonyl)-5-acetamidopentylurea |
| 47 | aminomalonic acid dimethyl ester | N-[4-(1-allyloxyiminomethyl)phenyl]-N'-bis(methoxycarbonyl)methylurea |
| 48 | (3-acetyl-5-imidazolyl)alanine | N-[4-(1-allyloxyiminomethyl)phenyl]-N'-(1-methoxycarbonyl)-2-(3-acetyl-5-imidazolyl)ethylurea | into cold water and extracted with diethyl ether. The ether solution is dried over $MgSO_4$ and filtered, and the solvent is removed by rotary evaporator to yield the product N-[4-(1-allyloxyiminoethyl)phenyl]-N'-phenoxycarbonylmethylurea.

EXAMPLES 31–48

The compounds in Table 2 are prepared by the following procedure: A solution of 0.02 mol p-aminoacetophenone in 40 mL THF is added dropwise to a solution of 0.02 mol of amino acid ester isocyanate and 5 mL pyridine in 40 mL THF, and the reaction mixture is stirred for 3 hours. The solvent is then removed by rotary evaporator. The residue is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to give the N-[4-(1-hydroxyiminoethyl)phenyl] urea.

A solution of the N-4-(1-hydroxyiminoethyl)phenyl] urea in 25% methanolic sodium methoxide (1.0 equivalent) is treated at room temperature with 1.1 equivalent of vinylic halide. The reaction mixture is stirred until the temperature falls to about 20° C. The reaction mixture is then poured into cold water and extracted with diethyl ether. The ether solution is dried over $MgSO_4$ and filtered, and the solvent is removed by rotary evaporator to yield the product N-[4-(1-allyloxyiminoethyl)phenyl] urea.

EXAMPLE 49

4-(allylamino)benzaldehyde ethylene glycol acetal is made as follows: A mixture of 0.2 mol 4-(allylamino)benzaldehyde (prepared as described by R. G. Shepherd in U.S. Pat. No. 4,281,019), 20 mL ethylene glycol, and 1.0 g p-toluenesulfonic acid in 200 mL toluene is heated with stirring to reflux under $N_2$ for 5 hours in a 500 mL round bottom flask equipped with a Dean-Stark trap and reflux condenser. During this time a mixture of water and ethylene glycol is collected in the trap. The product mixture is washed with saturated aqueous sodium bicarbonate solution and with water. The organic layer is dried over $MgSO_4$, and the solvent is distilled A solution of 0.1 of 4-(allylamino)benzaldehyde ethylene glycol acetal in 100 mL of anhydrous THF is added dropwise over 10 minutes to a solution of 0.1 mol of the glycine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-allyl-N-[4-(hydroxyiminomethyl)phenyl]-N'-methoxycarbonylmethylurea, is isolated by filtration and dried in vacuo.

EXAMPLE 50

A solution of 0.1 mol of 4-(allylamino)benzaldehyde ethylene glycol acetal in 100 mL of anhydrous THF is added dropwise over 10 minutes to a solution of 0.1 mol of the glycine ethyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-allyl-N-[4-(hydroxyiminomethyl)phenyl]-N'-ethoxycarbonylmethylurea, is isolated by filtration and dried in vacuo.

EXAMPLE 51

A solution of 0.1 mol of 4-(allylamino)benzaldehyde ethylene glycol acetal in 100 mL of anhydrous THF is added dropwise over 10 minutes to a solution of 0.1 mol of the glycine n-propyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. The product, N-allyl-N-[4-(hydroxyiminomethyl)phenyl]-N'-n-propoxycarbonylmethylurea, is isolated by filtration and dried in vacuo.

EXAMPLE 52

A solution of 0.1 mol of 4-(allylamino)benzaldehyde ethylene glycol acetal in 100 mL of anhydrous THF is added dropwise over 10 minutes to a solution of 0.1 mol of the glycine isopropyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. The product, N-allyl-N-[4-(hydroxyiminomethyl)phenyl]-N'-isopropoxycarbonylmethylurea, is isolated by filtration and dried in vacuo.

EXAMPLE 53

A solution of 0.1 mol of 4-(allylamino)benzaldehyde ethylene glycol acetal in 100 mL of anhydrous THF is added dropwise over 10 minutes to a solution of 0.1 mol of the glycine tert-butyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. The product, N-allyl-N-[4-(hydroxyiminomethyl)phenyl]-N'-tert-butoxycarbonylmethylurea, is isolated by filtration and dried in vacuo.

EXAMPLE 54

A solution of 0.1 mol of 4-(allylamino)benzaldehyde ethylene glycol acetal in 100 mL of anhydrous THF is added dropwise over 10 minutes to a solution of 0.1 mol of the glycine phenyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.1 mmol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. The product, N-allyl-N-4-(hydroxyiminomethyl)phenyl]-N'-phenoxycarbonylmethylurea, is isolated by filtration and dried in vacuo.

EXAMPLES 55–72

For the compounds in Table 3, the following procedure is followed: A solution of 0.1 mol of 4-(allylamino)benzaldehyde ethylene glycol acetal in 100 mL of anhydrous THF is added dropwise over 10 minutes to a solution of 0.1 mol of the amino acid methyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. The product N-allyl-N-[4-(hydroxyiminomethyl)phenyl] urea is isolated by filtration and dried in vacuo.

EXAMPLE 73

0.35 mol diphosgene is added dropwise over 1 hour to a mixture of 0.28 mol of methyl 2-amino-4-pentenoate, prepared as described by D. Ferroud, J. P. Genet, and R. Kiolle in *Tetrahedron Letters*, 1986, 27, 23–26, and 0.4 g activated charcoal in 400 mL dioxane under N₂. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give methyl 2-isocyanato-4-pentenoate.

TABLE 3

| Example | Amino Acid Methyl Ester Isocyanate | Product |
|---|---|---|
| 55 | alanine | N-allyl-N-[4-(allyloxyiminomethyl)phenyl]-N'-1-methoxycarbonylethylurea |
| 56 | valine | N-allyl-N-[4-(allyloxyiminomethyl)phenyl]-N'-(1-methoxycarbonyl)-2-methylpropylurea |
| 57 | leucine | N-allyl-N-[4-(allyloxyiminomethyl)phenyl]-N'-(1-methoxycarbonyl)-3-methylbutylurea |
| 58 | isoleucine | N-allyl-N-[4-(allyloxyiminomethyl)phenyl]-N'-(1-methoxycarbonyl)-1-methylbutylurea |
| 59 | phenylalanine | N-allyl-N-[4-(allyloxyiminomethyl)phenyl]-N'-(1-methoxycarbonyl)-2-phenylethylurea |
| 60 | (N-acetyl-3-indolyl)alanine | N-allyl-N-[4-(allyloxyiminomethyl)phenyl]-N'-(1-methoxycarbonyl)-2-(N-acetyl-3-indolyl)-ethylurea |
| 61 | methionine | N-allyl-N-[4-(allyloxyiminomethyl)phenyl]-N'-(1-methoxycarbonyl)-3-(methylthio)-propylurea |
| 62 | O-acetylserine | N-allyl-N-[4-(allyloxyiminomethyl)phenyl]-N'-(1-methoxycarbonyl)-2-acetyloxyethylurea |
| 63 | O-acetylthreonine | N-allyl-N-[4-(allyloxyiminomethyl)phenyl]-N'-(1-methoxycarbonyl)-2-acetyloxypropylurea |
| 64 | S-acetylcysteine | N-allyl-N-[4-(allyloxyiminomethyl)phenyl]-N'-(1-methoxycarbonyl)-2-acetylthioethylurea |
| 65 | O-acetyltyrosine | N-allyl-N-[4-(allyloxyiminomethyl)phenyl]-N'-(1-methoxycarbonyl)-2-(4-acetyloxyphenyl)urea |
| 66 | asparagine | N-allyl-N-[4-(allyloxyiminomethyl)phenyl]-N'-(1-methoxycarbonyl)-2-amidoethylurea |
| 67 | glutamine | N-allyl-N-[4-(allyloxyiminomethyl)phenyl]-N'-(1-methoxycarbonyl)-3-amidopropylurea |
| 68 | aspartic acid dimethyl ester | N-allyl-N-[4-(allyloxyiminomethyl)phenyl]-N'-1,2-bis(methoxycarbonyl)ethylurea |
| 69 | glutamic acid dimethyl ester | N-allyl-N-[4-(allyloxyiminomethyl)phenyl]-N'-1,3-bis(methoxycarbonyl)propylurea |
| 70 | ε-N-acetyllysine | N-allyl-N-[4-(allyloxyiminomethyl)phenyl]-N'-(1-methoxycarbonyl)-5-acetamidopentylurea |
| 71 | aminomalonic acid dimethyl ester | N-allyl-N-[4-(allyloxyiminomethyl)phenyl]-N'-bis(methoxycarbonyl)methylurea |
| 72 | (3-acetyl-5-imidazolyl)alanine | N-allyl-N-[4-(allyloxyiminomethyl)phenyl]-N'-(1-methoxycarbonyl)-2-(3-acetyl-5- |

TABLE 3-continued

| Example | Amino Acid Methyl Ester Isocyanate | Product |
|---|---|---|
| | | imidazolyl)ethylurea |

A solution of 0.1 mol of p-aminobenzaldehyde ethylene glycol acetal in 100 mL of anhydrous THF is added dropwise over 10 minutes to a solution of 0.1 mol of methyl 2-isocyanato-4-pentenoate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl]-N'-[1-(1-methoxycarbonyl)-3-butenyl]urea, is isolated by filtration and dried in vacuo.

EXAMPLE 74

0.35 mol diphosgene is added dropwise over 1 hour to a mixture of 0.28 mol of methyl 2-amino-4-methyl-4-pentenoate, prepared as described by D. Ferroud, J. P. Genet, and R. Kiolle in *Tetrahedron Letters*, 1986, 27, 23–26, and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF and the pH of the solution is adjusted to 5.5–6.0 by addition of pyridine. The product mixture is again filtered, and the product is purified by fractional distillation to give methyl 2-isocyanato-4-methyl-4-pentenoate.

A solution of 0.1 mol of p-aminobenzaldehyde ethylene glycol acetal in 100 mL of anhydrous THF is added dropwise over 10 minutes to a solution of 0.1 mol of methyl 2-isocyanato-4-methyl-4-pentenoate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl]-N'-[1-(1-methoxycarbonyl)-3-methyl-3-butenyl]urea, is isolated by filtration and dried in vacuo.

EXAMPLE 75

0.35 mol diphosgene is added dropwise over 1 hour to a mixture of 0.28 mol of methyl 2-amino-5-phenyl-4-pentenoate, prepared as described by D. Ferroud, J. P. Gene:, and R. Kiolle in *Tetrahedron Letters*, 1986, 27, 23–26, and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give methyl 2-isocyanato-5-phenyl-4-pentenoate.

A solution of 0.1 mol of p-aminobenzaldehyde ethylene glycol acetal in 100 mL of anhydrous THF is added dropwise over 10 minutes to a solution of 0.1 mol of methyl 2-isocyanato-5-phenyl-4-pentenoate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl-N'-1-(1-methoxycarbonyl)-4-phenyl-3-butenyl]urea, is isolated by filtration and dried in vacuo.

EXAMPLE 76

0.35 mol diphosgene is added dropwise over 1 hour to a mixture of 0.28 mol of methyl 2-amino-6-acetyloxy-4-hexenoate, prepared as described by D. Ferroud, J. P. Genet, and R. Kiolle in *Tetrahedron Letters*, 1986, 27, 23–26, and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give methyl 2-isocyanato-6-acetyloxy-4-hexenoate.

A solution of 0.1 mol of p-aminobenzaldehyde ethylene glycol acetal in 100 mL of anhydrous THF is added dropwise over 10 minutes to a solution of 0.1 mol of methyl 2-isocyanato-6-acetyloxy-4-hexenoate and 0.35 mol pyridine in 100 ml THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl]-N'-λ1-(1-methoxycarbonyl)-5-acetyloxy-3pentenyl]urea, is isolated by filtration and dried in vacuo.

EXAMPLE 77

A solution of 0.02 mol p-aminoacetophenone in 40 mL THF is added dropwise to a solution of 0.02 mol of methyl 2-isocyanato-4-pentenoate and 5 mL pyridine in 40 mL THF, and the reaction mixture is stirred for 3 hours. The solvent is then removed by rotary evaporator. The residue is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to give the product, N-[4-(1-hydroxyiminoethyl)phenyl]-N'-[1-(1-methoxycarbonyl)-3-butenyl]urea.

EXAMPLE 78

A solution of 0.02 mol p-aminoacetophenone in 40 mL THF is added dropwise to a solution of 0.02 mol of methyl 2-isocyanato-4-methyl-4-pentenoate and 5 mL pyridine in 40 mL THF, and the reaction mixture is stirred for 3 hours. The solvent is then removed by rotary evaporator. The residue is dispersed in 50 mL CH₃OH, and 1.53 g hydroxylamine hydrochloride and 6.4 g trimethyl orthoformate are added. The reaction mixture is heated to reflux for 1 hour. The solvent is removed by rotary evaporator to give the product, N-[4-(1-hydroxyiminoethyl)phenyl]-N'-[1-(1-methoxycarbonyl)-3-methyl-3-butenyl]urea.

EXAMPLE 79

A solution of 0.02 mol p-aminoacetophenone in 40 mL THF is added dropwise to a solution of 0.02 mol of methyl 2-isocyanato-5-phenyl-4-pentenoate and 5 mL pyridine in 40 mL THF, and the reaction mixture is stirred for 3 hours. The solvent is then removed by rotary evaporator. The residue is dispersed in 50 mL CH₃OH, and 1.53 g hydroxylamine hydrochloride and 6.4 g trimethyl orthoformate are added. The reaction mixture is heated to reflux for 1 hour. The solvent is removed by rotary evaporator to give the product, N-[4-(1-hydroxyiminoethyl)phenyl]-N'-[1-(1-methoxycarbonyl)-4-phenyl-3-butenyl]urea.

EXAMPLE 80

A solution of 0.02 mol p-aminoacetophenone in 40 mL THF is added dropwise to a solution of 0.02 mol of methyl 2-isocyanato-6-acetyloxy-4-hexenoate and 5 mL pyridine in 40 mL THF, and the reaction mixture is stirred for 3 hours. The solvent is then removed by rotary evaporator. The residue is dispersed in 50 mL CH₃OH, and 1.53 g hydroxylamine hydrochloride and 6.4 g trimethyl orthoformate are added. The reaction mixture is heated to reflux for 1 hour. The solvent is removed by rotary evaporator to give the product, N-[4-(1-hydroxyiminoethyl)phenyl-N'-[1-(1-methoxycarbonyl)-5-acetyloxy-3-pentenyl]urea.

EXAMPLE 81

0.35 mol diphosgene is added dropwise over 1 hour to a mixture of 0.28 mol of alanine allyl ester, prepared as described by H. Waldmann and H. Kunz in *Liebigs Ann. Chem.*, 1983, 1712–1725, and 0.4 g activated charcoal in 400 mL dioxane under N₂. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give alanine allyl ester isocyanate.

A solution of 0.1 mol of p-aminobenzaldehyde ethylene glycol acetal in 100 mL of anhydrous THF is added dropwise over 10 minutes to a solution of 0.1 mol of alanine allyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. The product, N-[4-(hydroxyiminomethyl)phenyl]-N'-[1-(allyloxycarbonyl)ethyl]urea, is isolated by filtration and dried in vacuo.

EXAMPLE 82

0.35 mol diphosgene is added dropwise over 1 hour to a mixture of 0.28 mol of glycine allyl ester, prepared as described by H. Waldmann and H. Kunz in *Liebigs Ann. Chem.*, 1983, 1712–1725, and 0.4 g activated charcoal in 400 mL dioxane under N₂. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give glycine allyl ester isocyanate.

A solution of 0.1 mol of p-aminobenzaldehyde ethylene glycol acetal in 100 mL of anhydrous THF is added dropwise over 10 minutes to a solution of 0.1 mol of glycine allyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. The product, N-[4-(hydroxyiminomethyl)phenyl-N'-allyloxycarbonylmethylurea, is isolated by filtration and dried in vacuo.

EXAMPLE 83

0.35 mol diphosgene is added dropwise over 1 hour to a mixture of 0.28 mol of isoleucine allyl ester, prepared as described by H. Waldmann and H. Kunz in *Liebigs Ann. Chem.*, 1983, 1712–1725, and 0.4 g activated charcoal in 400 mL dioxane under N₂. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give isoleucine allyl ester isocyanate.

A solution of 0.1 mol of p-aminobenzaldehyde ethylene glyco acetal in 100 mL of anhydrous THF is added dropwise over 10 minutes to a solution of 0.1 mol of isoleucine allyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. The product, N-[4-(hydroxyiminomethyl)- phenyl]-N'-[1-(allyloxycarbonyl)-1-methylbutyl]urea, is isolated by filtration and dried in vacuo.

EXAMPLE 84

0.35 mol diphosgene is added dropwise over 1 hour to a mixture of 0.28 mol of leucine allyl ester, prepared as described by H. Waldmann and H. Kunz in *Liebigs Ann. Chem.*, 1983, 1712–1725, and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF and the pH of the solution is adjusted to 5.5–6.0 by addition of pyridine. The product mixture is again filtered, and the product is purified by fractional distillation to give leucine allyl ester isocyanate.

A solution of 0.1 mol of p-aminobenzaldehyde ethylene glycol acetal in 100 mL of anhydrous THF is added dropwise over 10 minutes to a solution of 0.1 mol of leucine allyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl-N'-[1-(allyloxycarbonyl)-3methylbutyl]urea, is isolated by filtration and dried in vacuo.

EXAMPLE 85

0.35 mol diphosgene is added dropwise over 1 hour to a mixture of 0.28 mol of phenylalanine allyl ester, prepared as described by H. Waldmann and H. Kunz in *Liebigs Ann. Chem.*, 1983, 1712–1725, and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give phenylalanine allyl ester isocyanate.

A solution of 0.1 mol of p-aminobenzaldehyde ethylene glycol acetal in 100 mL of anhydrous THF is added dropwise over 10 minutes to a solution of 0.1 mol of phenylalanine allyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl]-N'-[1-(allyloxycarbonyl)-2-phenylethyl]urea, is isolated by filtration and dried in vacuo.

EXAMPLE 86

0.35 mol diphosgene is added dropwise over 1 hour to a mixture of 0.28 mol of valine allyl ester, prepared as described by H. Waldmann and H. Kunz in *Liebigs Ann. Chem.*, 1983, 1712–1725, and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the product is purified by fractional distillation to give valine allyl ester isocyanate.

A solution of 0.1 mol of p-aminobenzaldehyde ethylene glycol acetal in 100 mL of anhydrous THF is added dropwise over 10 minutes to a solution of 0.1 mol of valine allyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mmol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. The product, N-[4-(hydroxyiminomethyl)phenyl]-N'-[1-(allyloxycarbonyl)-2-methylpropyl]urea, is isolated by filtration and dried in vacuo.

EXAMPLE 87

A solution of 0.02 mol p-aminoacetophenone in 40 mL THF is added dropwise to a solution of 0.02 mol of alanine allyl ester isocyanate and 5 mL pyridine in 40 mL THF, and the reaction mixture is stirred for 3 hours. The solvent is then removed by rotary evaporator. The residue is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to give the product, N-[4-(1-hydroxyiminoethyl)phenyl]-N'-[1-(allyloxycarbonyl)ethyl]urea.

EXAMPLE 88

A solution of 0.02 mol p-aminoacetophenone in 40 mL THF is added dropwise to a solution of 0.02 mol of glycine allyl ester isocyanate and 5 mL pyridine in 40 mL THF, and the reaction mixture is stirred for 3 hours. The solvent is then removed by rotary evaporator. The residue is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to give the product, N-[4-(1-hydroxyiminoethyl)-phenyl] -N'-allyloxycarbonylmethylurea.

EXAMPLE 89

A solution of 0.02 mol p-aminoacetophenone in 40 mL THF is added dropwise to a solution of 0.02 mol of isoleucine allyl ester isocyanate and 5 mL pyridine in 40 mL THF, and the reaction mixture is stirred for 3 hours. The solvent is then removed by rotary evaporator. The residue is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to give the product, N-[4-(1-hydroxyiminoethyl)phenyl]-N'-[1-(allyloxycarbonyl)-1-methylbutyl]urea.

EXAMPLE 90

A solution of 0.02 mol p-aminoacetophenone in 40 mL THF is added dropwise to a solution of 0.02 mol of leucine allyl ester isocyanate and 5 mL pyridine in 40 mL THF, and the reaction mixture is stirred for 3 hours. The solvent is then removed by rotary evaporator. The residue is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to give the product N-[4-(1-hydroxyiminoethyl)phenyl]-N'-[1-(allyloxycarbonyl)-3-methylbutyl]urea.

EXAMPLE 91

A solution of 0.02 mol p-aminoacetophenone in 40 mL THF is added dropwise to a solution of 0.02 mol of phenylalanine allyl ester isocyanate and 5 mL pyridine in 40 mL THF, and the reaction mixture is stirred for 3 hours. The solvent is then removed by rotary evaporator. The residue is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to give the product, N-[4-(1-hydroxyiminoethyl)phenyl]-N'-[1-(allyloxycarbonyl)-2-phenylethyl]urea.

EXAMPLE 92

A solution of 0.02 mol p-aminoacetophenone in 40 mL THF is added dropwise to a solution of 0.02 mol of valine allyl ester isocyanate and 5 mL pyridine in 40 mL THF, and the reaction mixture is stirred for 3 hours. The solvent is then removed by rotary evaporator. The residue is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to give the product, N-[4-(1-hydroxyiminoethyl)phenyl]-N'-[1-(allyloxycarbonyl)-2-methylpropyl]urea.

EXAMPLE 93

A solution of 0.02 mol N-allylglycine ethyl ester, prepared as described by S. B. Hyeon, I. Nagai, H. Iesaka, T. Kajita, and M. Furushima in European Patent Application No. 181,494, in 40 mL of THF is added dropwise to a solution of 0.02 mol of 4-isocyanatoacetophenone, prepared as described by E. E. Kilbourn, D. L. Peardon, and J. E. Ware in U.S. Pat. No. 3,931,203, and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-allyl-N'-ethoxycarbonylmethylurea.

EXAMPLE 94

A solution of 0.02 mol N-allylalanine ethyl ester, prepared as described by S. B. Hyeon, I. Nagai, H. Iesaka, T. Kajita, and M. Furushima in European Patent Application No. 181,494, in 40 mL of THF is added dropwise to a solution of 0.02 mol of 4-isocyanatopropiophenone, prepared as described by E. E. Kilbourn, D. L. Peardon, and J. E. Ware in U.S. Pat. No. 3,931,203, and 5 mL of pyridine in 40 ml of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminopropyl)phenyl]-N'-allyl-N'-(1-ethoxycarbonylethyl)urea.

EXAMPLE 95

A solution of 0.02 mol N-2-butenylglycine ethyl ester, prepared as described by S. B. Hyeon, I. Nagai, H. Iesaka, T. Kajita, and M. Furushima in European Patent Application No. 181,494, in 40 mL of THF is added dropwise to a solution of 0.02 mol of 4-isocyanatobutyrophenone, prepared as described by E. E. Kilbourn, D. L. Peardon, and J. E. Ware in U.S. Pat. No. 3,931,203, and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminobutyl)phenyl]-N'-(2-butenyl)-N'-ethoxycarbonylmethylurea.

EXAMPLE 96

A solution of 0.02 mol N-(2-styryl)glycine ethyl ester, prepared as described by A. Padwa, R. Lim, J. G. MacDonald, H. L. Gingrich, and S. M. Kellar in *J. Org. Chem.*, 1985, 50, 3816–3823, in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-4-(1hydroxyiminoethyl)phenyl]-N'-(2-styryl)-N'-ethoxycarbonylmethylurea.

EXAMPLE 97

A solution of 0.02 mol N-(2-styryl)alanine ethyl ester, prepared as described by A. Padwa, R. Lim, J. G. MacDonald, H. L. Gingrich, and S. M. Kellar in *J. Org. Chem.*, 1985, 50, 3816–3823, in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-(2-styryl)-N'-ethoxycarbonyl)ethylurea.

EXAMPLE 98

A solution of 0.02 mol N-(allyloxycarbonyl)-phenylalanine benzyl ester, prepared as described by F.

Guibe, O. Dangles, and G. Balavione in *Tetrahedron Letters*, 1986, 27, 2365–2368, in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH3OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-allyloxycarbonyl-N'-(1-benzyloxycarbonyl)-2-phenylethylurea.

EXAMPLE 99

A solution of 0.02 mol N-(altyloxycarbonyl)-0-tert-butylserine tert-butyl ester, prepared as described by F. Guibe, O. Dangles, and G. Balavione in *Tetrahedron Letters*, 1986, 27, 2365–2368, in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH3OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-allyloxycarbonyl-N'-(1-tert-butyloxycarbonyl)-2-tert-butoxyethylurea.

EXAMPLE 100

A solution of 0.06 mol of N-(2-allylphenyl)alanine, prepared as described by A. Padwa, H. L. Gingrich, and R. Lim in *J. Org. Chem.*, 1982, 47, 2447–2456, and 0.066 mol of HCl in 100 mL of CH3OH is stirred at reflux for 8 hours. The solution is then cooled and treated with 0.066 mol of sodium bicarbonate. The solvent is removed by rotary evaporator, and the residue is dissolved in diethyl ether, filtered, dried over MgSO4, and filtered. The solvent is removed by rotary evaporator to give N-(2-allylphenyl)alanine methyl ester.

A solution of 0.02 mol N-(2-allylphenyl)alanine methyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH3OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl,phenyl]-N'-(2-allylphenyl)-N'-(1-methoxycarbonyl)ethylurea.

EXAMPLE 101

A solution of 0.06 mol of N-(2-allylphenyl)phenylglycine, prepared as described by A. Padwa, H. L. Gingrich, and R. Lim in *J. Org. Chem.*, 1982, 47, 2447–2456, and 0.066 mol of HCl in 100 mL of CH3OH is stirred at reflux for 8 hours. The solution is then cooled and treated with 0.066 mol of sodium bicarbonate. The solvent is removed by rotary evaporator, and the residue is dissolved in diethyl ether, filtered, dried over MgSO4, and filtered. The solvent is removed by rotary evaporator to give N-(2-allylphenyl)phenylglycine methyl ester.

A solution of 0.02 mol N-(2-allylphenyl)phenylglycine methyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH3OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-(2-allylphenyl)-N'-(methoxycarbonyl)phenylmethylurea.

EXAMPLE 102

A solution of 0.06 mol of N-(2-allylphenyl)glycine, prepared as described by A. Padwa, R. Lim, J. G. MacDonald, H. L. Gingrich, and S. M. Kellar in *J. Org. Chem.*, 1985, 50, 3816–3823, and 0.066 mol of HCl in 100 mL of CH3OH is stirred at reflux for 8 hours. The solution is then cooled and treated with 0.066 mol of sodium bicarbonate. The solvent is removed by rotary evaporator, and the residue is dissolved in diethyl ether, filtered, dried over MgSO4, and filtered. The solvent is removed by rotary evaporator to give N-(2-allylphenyl)glycine methyl ester.

A solution of 0.02 mol N-(2-allylphenyl)glycine methyl ester in 40 mL of THF is added dropwise to a solution of 0.02 mol of 4- isocyanaioacetophenone and 5 mL of pyridine in 40 mL of THF, and the reaction mixture is stirred for 3 hours. The solvent is then removed by rotary evaporator. The residue is dispersed in 50 mL of CH3OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-(2-allylphenyl)-N'-methoxycarbonylmethylurea.

EXAMPLE 103

A solution of 0.06 mol of N-(allyloxycarbonyl)alanine, prepared as described by H. Kunz and C. Unverzagt in *Angew. Chem. Int. Ed. Engl.*, 1984, 23, 436–437, and 0.066 mol of HCl in 100 mL of CH3OH is stirred at reflux for 8 hours. The solution is then cooled and treated with 0.066 mol of sodium bicarbonate. The solvent is removed by rotary evaporator, and the residue is dissolved in diethyl ether, filtered, dried over MgSO4, and filtered. The solvent is removed by rotary evaporator to give N-(allyloxycarbonyl)alanine methyl ester.

A solution of 0.02 mol N-(allyloxycarbonyl)alanine methyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH3OH, and 0.02 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]N'-allyloxycarbonyl-N'-(1-methoxycarbonyl)ethylurea.

EXAMPLE 104

A solution of 0.06 mol of N-(allyloxycarbonyl)phenylalanine, prepared as described by H. Kunz and C. Unverzagt in *Angew. Chem. Int. Ed. Engl.*, 1984, 23, 436–437, and 0.066 mol of HCl in 100 mL of CH3OH is stirred at reflux for 8 hours. The solution is then cooled and treated with 0.066 mol of sodium bicarbonate. The solvent is removed by rotary evaporator, and the residue is dissolved in diethyl ether, filtered, dried over MgSO4, and filtered. The solvent is removed by rotary evaporator to give N-(allyloxycarbonyl)phenylalanine methyl ester.

A solution of 0.02 mol N-(allyloxycarbonyl)phenylalanine methyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH3OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethylphenyl]-N'-allyloxycarbonyl-N'-(1-methoxycarbonyl)- 2-phenylethyl]urea.

EXAMPLE 105

A solution of 0.06 mol of N-(allyloxycarbonyl)methionine, prepared as described by H. Kunz and C. Unverzagt in *Angew. Chem. Int. Ed. Engl.*, 1984, 23, 436–437, and 0.066 mol of HCl in 100 mL of CH3OH is stirred at reflux for 8 hours. The solution is then cooled and treated with 0.066 mol of sodium bicarbonate. The solvent is removed by rotary evaporator, and the residue is dissolved in diethyl ether, filtered, dried over MgSO4, and filtered. The solvent is removed by rotary evaporator to give N-(allyloxycarbonyl)methionine methyl ester.

A solution of 0.02 mol N-(allyloxycarbonyl)methionine methyl ester in 40 mL of THF is added dropwise to a solution of 0.02 mol of 4isocyanatoacetophenone and 5 mL of pyridine in 40 mL of THF, and the reaction mixture is stirred for 3 hours. The solvent is then removed by rotary evaporator. The residue is dispersed in 50 mL of CH3OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-allyloxycarbonyl-N'-[(1- methoxycarbonyl)-3-(methylthio)propyl]urea.

EXAMPLE 106

A solution of 0.06 mol of N-(allyloxycarbonyl)glycine, prepared as described by F. Guibe, O. Dangles, and G. Balavione in *Tetrahedron Letters*, 1986, 27, 2365–2368, and 0.066 mol of HCl in 100 mL of CH3OH is stirred at reflux for 8 hours. The solution is then cooled and treated with 0.066 mol of sodium bicarbonate. The solvent is removed by rotary evaporator, and the residue is dissolved in diethyl ether, filtered, dried over MgSO4, and filtered. The solvent is removed by rotary evaporator to give N-(allyloxycarbonyl)glycine methyl ester.

A solution of 0.02 mol N-(allyloxycarbonyl)glycine methyl ester in 40 mL of THF is added dropwise to a solution of 0.02 mol of 4isocyanatoacetophenone and 5 mL of pyridine in 40 mL of THF, and the reaction mixture is stirred for 3 hours. The solvent is then removed by rotary evaporator. The residue is dispersed in 50 mL of CH3OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-allyloxycarbonyl-N'methoxycarbonylmethylurea.

EXAMPLE 107

A solution of 0.06 mol of N-(allyloxycarbonyl)leucine, prepared as described by F. Guibe, O. Dangles, and G. Balavione in *Tetrahedron Letters*, 1986, 27, 2365–2368, and 0.066 mol of HCl in 100 mL of CH3OH is stirred at reflux for 8 hours. The solution is then cooled and treated with 0.066 mol of sodium bicarbonate. The solvent is removed by rotary evaporator, and the residue is dissolved in diethyl ether, filtered, dried over MgSO4, and filtered. The solvent is removed by rotary evaporator to give N-(allyloxycarbonyl)leucine methyl ester A solution of 0.02 mol N-(allyloxycarbonyl)leucine methyl ester in 40 mL of THF is added dropwise to a solution of 0.02 mol of 4isocyanatoacetophenone and 5 mL of pyridine in 40 mL of THF, and the reaction mixture is stirred for 3 hours. The solvent is then removed by rotary evaporator. The residue is dispersed in 50 mL of CH3OH, and 0.022 mol of hydroxylamine hydrochloride and 0.06 mol of trimethyl orthofurmate are added. The reaction mixture is heated to reflux for 1 hour. The solvent is removed by rotary evaporator to give the product, N-[4-(1-hydroxyiminoethyl)phenyl]-N'-allyloxycarbonyl-N']-(1-methoxycarbonyl)-3-methylbutyl]urea.

EXAMPLE 108

A solution of 0.02 mol methyl 2-amino-4-pentenoate in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH3OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-[(1-methoxycarbonyl)-3-butenyl]urea.

EXAMPLE 109

A solution of 0.02 mol methyl 2-amino-4-methyl-4-pentenoate in 40 mL of THF is added dropwise to a solution of 0.02 mol of 4isocyanatoacetophenone and 5 mL of pyridine in 40 mL of THF, and the reaction mixture is stirred for 3 hours. The solvent is then removed by rotary evaporator. The residue is dispersed in 50 mL of CH3OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-[(1-methoxycarbonyl)-3-methyl-3-butenyl]urea.

EXAMPLE 110

A solution of 0.02 mol methyl 2-amino-5-phenyl-4-pentenoate in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of CH3OH, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-[(1-methoxycarbonyl)-4-phenyl-3-butenyl]urea.

EXAMPLE 111

A solution of 0.02 mol methyl 2-amino-6-acetyloxy-4-hexenoate in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-[(1-methoxycarbonyl)-5-acetyloxy-3-pentenyl]urea.

EXAMPLE 112

A solution of 0.02 mol alanine allyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1hydroxyiminoethyl)phenyl]-N'-(1-allyloxycarbonyl)ethylurea.

EXAMPLE 113

A solution of 0.02 mol phenylalanine allyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1 hydroxyiminoethyl)phenyl]-N'-(1-allyloxycarbonyl)-2phenylethylurea.

EXAMPLE 114

A solution of 0.02 mol glycine allyl ester in 40 mL of THF is added dropwise to a solution of 0.02 mol of 4-isocyanatoacetophenone and 5 mL of pyridine in 40 mL of THF and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-allyloxycarbonylmethylurea.

EXAMPLE 115

A solution of 0.02 mol isoleucine allyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1-hydroxyiminoethyl)phenyl]-N'-(1-allyloxycarbonyl)-1-methylbutylurea.

EXAMPLE 116

A solution of 0.02 mol leucine allyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1hydroxyiminoethyl)phenyl]-N'-(1-allyloxycarbonyl)-3-methylbutylurea.

EXAMPLE 117

A solution of 0.02 mol valine allyl ester in 40 mL of THF is added dropwise to a solution of 0.02 mol of 4-isocyanatoacetophenone and 5 mL of pyridine in 40 mL of THF, and the reaction mixture is stirred for 3 hours. The solvent is then removed by rotary evaporator. The residue is dispersed in 50 mL of $CH_3OH$, and 0.022 mol of hydroxylamine hydrochloride and 0.06 mol of trimethyl orthoformate are added. The reaction mixture is heated to reflux for 1 hour. The solvent is removed by rotary evaporator to give the product, N-[4-(1hydroxyiminoethyl)phenyl]-N'-(1-allyloxycarbonyl)-2-methylpropylurea.

EXAMPLE 118

A solution of AIBN (0.001 mol) and N-[4(allyloxyiminomethyl)phenyl]-N'-methoxycarbonylmethylurea (0.01 mol) in 10 mL of toluene is stirred under a nitrogen atmosphere at 80° C. for 48 hours. The solvent is removed to leave a polymeric material.

EXAMPLE 119

A solution of AIBN (0.001 mol) and N-allyl-N-[4-(hydroxyiminomethyl)phenyl]-N'-methoxycarbonylmethylurea (0.01 mol) in 10 mL of toluene is stirred under a nitrogen atmosphere at 80° C. for 48 hours. The solvent is removed to leave a polymeric material.

EXAMPLE 120

A solution of AIBN (0.001 mol) and N-[-4-(hydroxyiminomethyl)phenyl]-N'-[1-(1-methoxycarbonyl)-3-butenyl]urea (0.01 mol) in 10 mL of toluene is stirred under a nitrogen atmosphere at 80° C. for 48 hours. The solvent is removed to leave a polymeric material.

EXAMPLE 121

A solution of AIBN (0.001 mol) and N-[4-(hydroxyiminomethyl)phenyl]-N'-allyloxycarbonylmethylurea (0.01 mol) in 10 mL of toluene is stirred under a nitrogen atmosphere at 80° C. for 48 hours. The solvent is removed to leave a polymeric material.

EXAMPLE 122

A solution of AIBN (0.001 mol) and N-[4-(hydroxyiminomethyl)phenyl]-N'-allyl-N'-ethoxycarbonylmethylurea (0.01 mol) in 10 mL of toluene is stirred under a nitrogen atmosphere at 80° C. for 48 hours. The solvent is removed to leave a polymeric material.

EXAMPLE 123

A solution of AIBN (0.001 mol) and N-[4-(1-hydroxyiminoethyl)phenyl]-N'-allyloxycarbonyl-N'methoxycarbonylmethylurea (0.01 mol) in 10 mL of toluene is stirred under a nitrogen atmosphere at 80° C. for 48 hours. The solvent is removed to leave a polymeric material.

As will be evident to those skilled in the art, various modifications of this invention can be made or followed in the light of the foregoing disclosure and discussion without departing from the spirit and scope of the disclosure or from the scope of the claims.

We claim:

1. A compound of the formula,

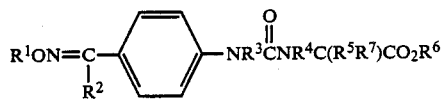

where each of $R^1$, $R^2$, $R^3$, $R^4$, $R^5$, $R^6$ and $R^7$ has zero to 10 C atoms, and no acetylenic unsaturation; each of $R^1$, $R^2$, $R^3$ and $R^4$ is independently selected from H and hydrocarbyl; with the proviso that $R^6$ is $C_1$-$C_{10}$ hydrocarbyl; each of $R^5$ and $R^7$ is independently selected from H, hydrocarbyl and hydrocarbyl substituted with a group selected from:

hydrocarbylcarbonylamino, di(hydrocarbylcarbonyl)amino, N-hydrocarbylcarbonyl(N-hydrocarbyl)amino, formylamino, diformylamino, and formyl(N-hydrocarbyl)amino, hydrocarbyloxy, hydrocarbylthio, formyl, formylthio, hydrocarbylcarbonyloxy, hydrocarbylcarbonylthio, hydrocarbylcarboxyl, hydrocarbylthiocarboxyl, hydrocarbylamino, dihydrocarbylamino, hydrocarbylcarbonyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbylcarbonyl)imidazolyl, and 5-(3-formyl)imidazoly; and where at least one of $R^1$, $R^2$, $R^3$, $R^4$, $R^5$, $R^6$ and $R^7$ contains olefinic unsaturation.

* * * * *

UNITED STATES PATENT AND TRADEMARK OFFICE
CERTIFICATE OF CORRECTION

PATENT NO. : 4,977,272
DATED : Dec. 11, 1990
INVENTOR(S) : Mark C. Cesa, et al

It is certified that error appears in the above-identified patent and that said Letters Patent is hereby corrected as shown below:

Column 32, line 26 & 27

In claim 1, line 21, after "5-imidazolyl", insert --- 5-(3-hydrocarbyl)imidazolyl, ---.

Signed and Sealed this

Fifth Day of May, 1992

Attest:

DOUGLAS B. COMER

Attesting Officer

Acting Commissioner of Patents and Trademarks